(12) United States Patent
Mernøe

(10) Patent No.: US 7,220,248 B2
(45) Date of Patent: May 22, 2007

(54) FLEXIBLE PISTON ROD

(75) Inventor: Morten Mernøe, Charlottenlund (DK)

(73) Assignee: M2 Medical A/S, Gentofte (DK)

( * ) Notice: Subject to any disclaimer, the term of this patent is extended or adjusted under 35 U.S.C. 154(b) by 0 days.

(21) Appl. No.: 11/158,277

(22) Filed: Jun. 21, 2005

(65) Prior Publication Data

US 2005/0251097 A1    Nov. 10, 2005

Related U.S. Application Data

(63) Continuation of application No. PCT/DK03/00915, filed on Dec. 19, 2003.

(51) Int. Cl.
*A61M 5/315* (2006.01)

(52) U.S. Cl. ...................... 604/218; 604/224

(58) Field of Classification Search ............... 604/218, 604/187, 111, 207, 191, 228, 210, 224
See application file for complete search history.

(56) References Cited

U.S. PATENT DOCUMENTS

| | | |
|---|---|---|
| 3,886,938 A | 6/1975 | Szabo et al. |
| 4,077,405 A | 3/1978 | Haerten et al. |
| 4,231,368 A | 11/1980 | Becker |
| 4,300,554 A | 11/1981 | Hessberg et al. |
| 4,313,439 A | 2/1982 | Babb et al. |
| 4,398,908 A | 8/1983 | Siposs |
| 4,435,173 A | 3/1984 | Siposs et al. |
| 4,443,218 A | 4/1984 | DeCant, Jr. et al. |
| 4,493,704 A | 1/1985 | Beard et al. |
| 4,529,401 A | 7/1985 | Leslie et al. |
| 4,850,817 A | 7/1989 | Nason et al. |
| 5,088,981 A | 2/1992 | Howson et al. |
| 5,190,522 A | 3/1993 | Wojcicki et al. |
| 5,314,412 A | 5/1994 | Rex |
| 5,342,180 A | 8/1994 | Daoud |
| 5,395,340 A | 3/1995 | Lee |
| 5,411,487 A * | 5/1995 | Castagna ..................... 604/198 |
| 5,551,850 A | 9/1996 | Williamson et al. |
| 5,569,186 A | 10/1996 | Lord et al. |
| 5,626,566 A | 5/1997 | Petersen et al. |
| 5,637,095 A | 6/1997 | Nason et al. |

(Continued)

FOREIGN PATENT DOCUMENTS

CA       2543545       5/2005

(Continued)

*Primary Examiner*—Kevin C. Sirmons
*Assistant Examiner*—Bhisma Mehta
(74) *Attorney, Agent, or Firm*—Fish & Richardson P.C.

(57) ABSTRACT

A flexible piston rod includes a piston and a row of elements, each having top, bottom, and lateral surfaces, the top surface of one element being connected to the bottom surface of an adjacent element by a hinge that allows the two adjacent elements to pivot from a first position, where a portion of the top surface of one element abuts a corresponding portion of the bottom surface of the adjacent element and corresponding to a rectilinear, relatively stiff configuration of the piston rod, to a second position wherein the top surface of one element is spaced from the bottom surface of the adjacent element and corresponding to a curved configuration of the piston rod. The lateral surface of each element has first and second mutually-opposed cylindrical surface portions incorporating a thread for meshing with a corresponding thread of an actuator for displacing the piston rod longitudinally.

10 Claims, 5 Drawing Sheets

U.S. PATENT DOCUMENTS

| | | |
|---|---|---|
| 5,665,065 A | 9/1997 | Colman et al. |
| 5,741,216 A | 4/1998 | Hemmingsen et al. |
| 5,772,635 A | 6/1998 | Dastur et al. |
| 5,919,167 A | 7/1999 | Mulhauser et al. |
| 5,925,018 A | 7/1999 | Ungerstedt |
| 5,928,201 A | 7/1999 | Poulsen et al. |
| 5,947,934 A | 9/1999 | Hansen et al. |
| 5,951,530 A | 9/1999 | Steengaard et al. |
| 5,957,889 A | 9/1999 | Poulsen et al. |
| 5,984,894 A | 11/1999 | Poulsen et al. |
| 5,984,897 A | 11/1999 | Petersen et al. |
| 5,997,475 A | 12/1999 | Bortz |
| 6,003,736 A | 12/1999 | Ljunggren |
| 6,010,485 A | 1/2000 | Buch-Rasmussen et al. |
| 6,033,377 A | 3/2000 | Rasmussen et al. |
| 6,045,537 A | 4/2000 | Klitmose |
| 6,074,372 A | 6/2000 | Hansen |
| 6,110,149 A | 8/2000 | Klitgaard et al. |
| 6,156,014 A | 12/2000 | Petersen et al. |
| 6,231,540 B1 | 5/2001 | Smedegaard |
| 6,248,067 B1 | 6/2001 | Causey, III et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 * | 10/2001 | Klitgaard ............... 604/218 |
| 6,379,339 B1 | 4/2002 | Klitgaard et al. |
| 6,381,496 B1 | 4/2002 | Meadows et al. |
| 6,427,088 B1 | 7/2002 | Bowman, IV et al. |
| 6,461,331 B1 | 10/2002 | Van Antwerp |
| 6,474,219 B2 * | 11/2002 | Klitmose et al. ............. 92/137 |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman IV et al. |
| 6,960,192 B1 | 11/2005 | Flaherty |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larsen et al. |
| 7,014,625 B2 | 3/2006 | Bengtsson |
| 7,018,360 B2 | 3/2006 | Flaherty et al. |
| 7,025,743 B2 | 4/2006 | Mann |
| 7,029,455 B2 | 4/2006 | Flaherty |
| 7,054,836 B2 | 5/2006 | Christensen et al. |
| 7,104,972 B2 | 9/2006 | Møller et al. |
| 7,133,329 B2 | 11/2006 | Skyggebjerg et al. |
| 2002/0004651 A1 | 1/2002 | Ljndggreen et al. |
| 2002/0007154 A1 * | 1/2002 | Hansen et al. ............. 604/207 |
| 2002/0040208 A1 | 4/2002 | Flaherty et al. |
| 2002/0091358 A1 * | 7/2002 | Klitmose ................... 604/131 |
| 2003/0055380 A1 | 3/2003 | Flaherty |
| 2003/0199825 A1 | 10/2003 | Flaherty |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |

| | | |
|---|---|---|
| 2004/0153032 A1 | 8/2004 | Garribotto et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0090808 A1 | 4/2005 | Malave et al. |
| 2005/0171512 A1 | 8/2005 | Flaherty |
| 2005/0182366 A1 | 8/2005 | Vogt et al. |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | DiIanni et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |

FOREIGN PATENT DOCUMENTS

| | | |
|---|---|---|
| EP | 0 496 141 A1 | 7/1992 |
| EP | 0 580 723 | 10/1995 |
| EP | 0 721 358 | 5/2002 |
| EP | 1 495 775 | 1/2005 |
| EP | 1 527 792 | 5/2005 |
| GB | 747 701 | 4/1956 |
| GB | 2 218 831 | 11/1989 |
| WO | WO-01/72360 A1 | 10/2001 |
| WO | WO 2005/072795 | 8/2005 |

* cited by examiner

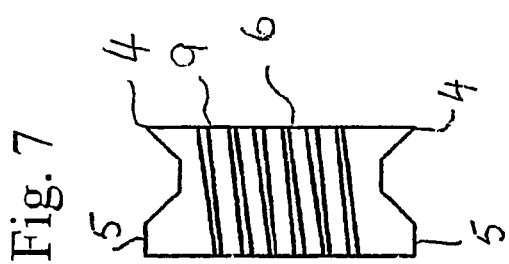
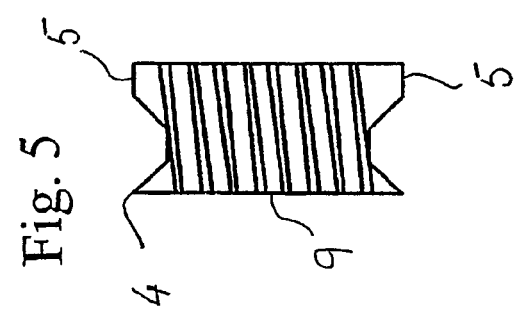
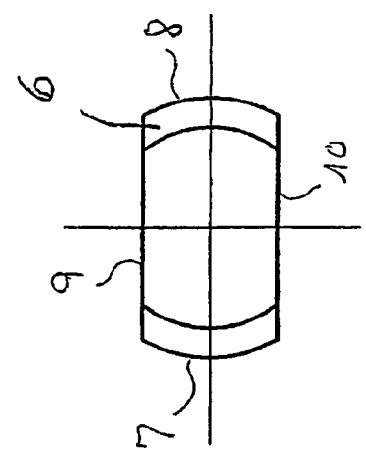

FLEXIBLE PISTON ROD

CROSS-REFERENCE TO RELATED APPLICATION

This application is a Continuation of co-pending International Application No. PCT/DK2003/000915, filed Dec. 19, 2003, the disclosure of which is incorporated herein by reference.

FEDERALLY SPONSORED RESEARCH OR DEVELOPMENT

Not Applicable

BACKGROUND OF THE INVENTION

The present invention relates to a flexible piston rod, particularly for use in medicine dispensing devices.

So as to render devices and applications where a piston rod is to linearly displace an object more compact it is desirable to avoid the space requirements necessary for allowing a rigid rectilinear piston rod to travel the entire displacement length along its axis. Several flexible piston rods have been conceived embodying a coil spring supported by an internal curved mandrel or guide rod or various elements collaborating with one another. All the known flexible piston rods are either too complicated or require relatively large forces to be displaced.

SUMMARY OF THE INVENTION

An object of the present invention is to provide a flexible piston rod that is simple to manufacture and operate and requires relatively small displacement forces.

According to the invention this object is achieved by the piston rod comprising a row of elements each having a top surface and a bottom surface as well as a lateral surface, the top surface of one element being connected to the bottom surface of the adjacent element by a hinge means located and adapted to allow the two adjacent elements to pivot from a first position where at least a portion of a top surface of one element abuts a corresponding portion of the bottom surface of the adjacent element, said first position corresponding to a rectilinear, relatively stiff configuration of the piston rod, to a second position wherein said top surface of one element is spaced from said bottom surface of the adjacent element corresponding to a curved configuration of said flexible piston rod.

In the currently preferred embodiment of a flexible piston rod according to the invention, said lateral surface has first and a second mutually opposed circular cylindrical surface portions incorporating a screw thread for meshing with a corresponding screw thread of an actuator for displacing the piston rod in the longitudinal direction thereof. Hereby a simple displacement mechanism which is self supporting and self centering is achieved.

Preferably, at least one surface portion disposed between said first and second surface portion is a plane so as to allow co-operation with means to prevent rotation of the piston rod around the longitudinal axis thereof when said screw threads on the lateral surface of said elements are engaged by said actuator screw threads.

Preferably, said portions of said top and bottom surfaces are spaced from said hinge. Hereby a particularly stable rectilinear configuration of the piston rod is achieved.

Advantageously, said elements and said hinges form an integrally molded piston rod molded in one piece from a moldable material, preferably a plastic material such as Nylon or POM.

In another aspect, the present invention relates to a flexible piston rod comprising a strip of relatively stiff and resilient material such as steel having in the relaxed state an arcuate cross section taken transversely to the longitudinal direction of said strip, a longitudinal row of evenly space apertures being provided along the length of said strip for receiving projection of an actuator for displacing said strip in the longitudinal direction thereof, and preferably the major portion of the said strip is rolled into a roll when the piston rod is in its least extended condition.

BRIEF DESCRIPTION OF THE DRAWINGS

In the following, the invention will be described and explained more in detail with reference to embodiments thereof shown, solely by way of example, in the accompanying drawings, where.

DETAILED DESCRIPTION OF THE INVENTION

Figure 1:
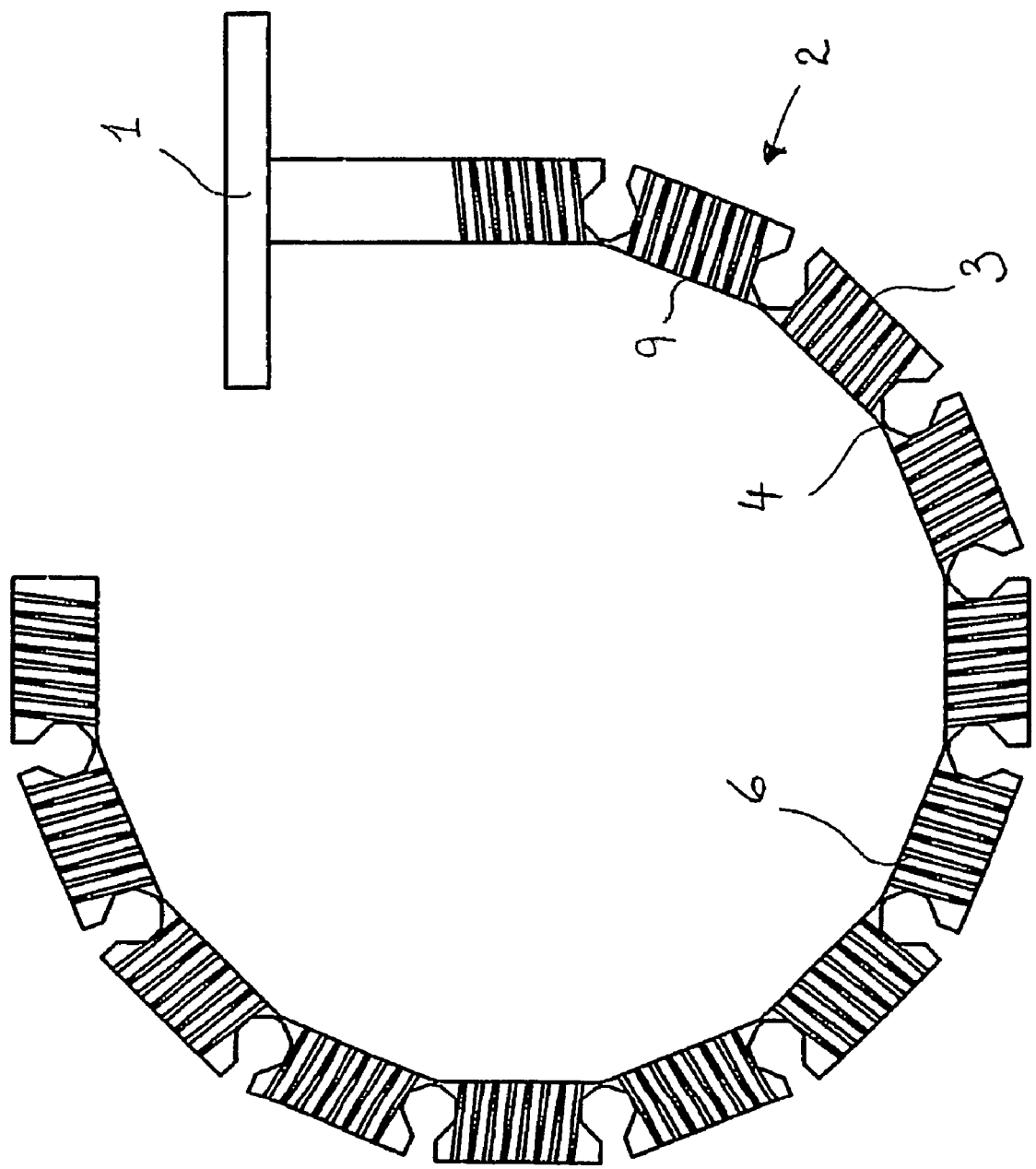
FIG. 1 is a schematic view of a first embodiment of a flexible piston rod according to the invention.
Figure 4:
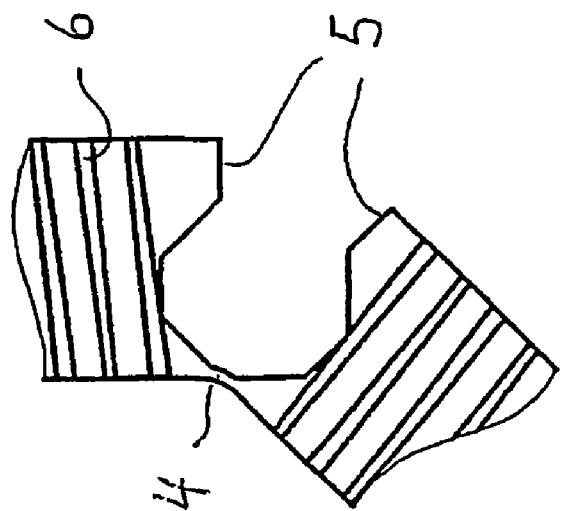
FIGS. 2-4 are schematic enlarged scale views of the hinge mechanism of the flexible piston rod according to FIG. 1, FIGS. 5-8 are schematic enlarged scale views from different angles of an element of the flexible piston rod of FIG. 1.
Figure 3:
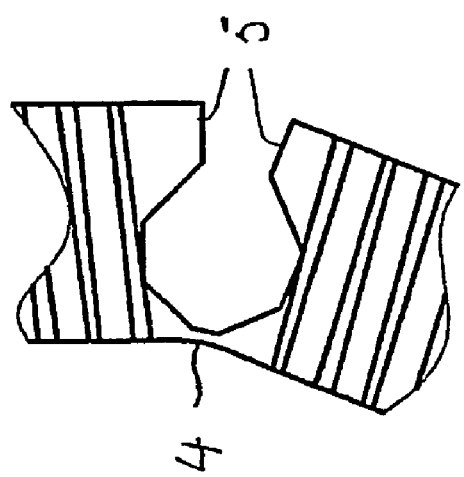
Figure 2:
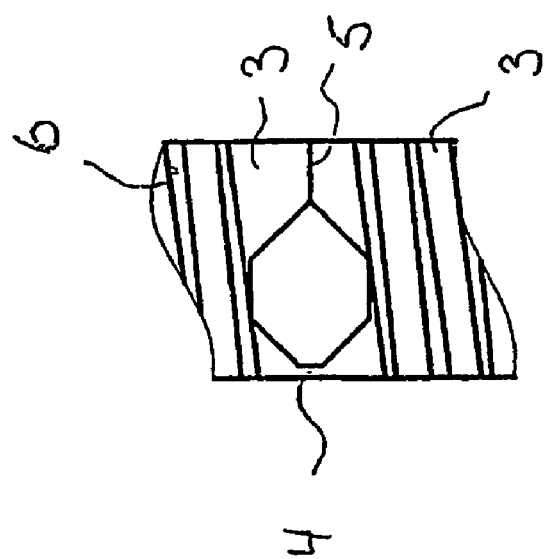

Referring now to FIGS. 1-8, a piston 1 is attached to one end of a flexible piston rod 2 constituted by a series of elements 3 interconnected by hinges 4. The elements 3 are integral with each other by means of the hinges 4 which allow mutually adjacent elements to pivot relative to one another from the position abutting one another shown in FIG. 2 wherein the elements 3 together form a rectilinear piston rod with abutment surfaces 5 and hinges 4 affording rigidity and thus rendering the piston rod 2 capable of exerting a pressure on the piston 1 without deflecting laterally, to the position shown in FIG. 4 wherein the elements 3 are pivoted way from one another so as to allow the curvature of the piston rod 2.

Figure 9:
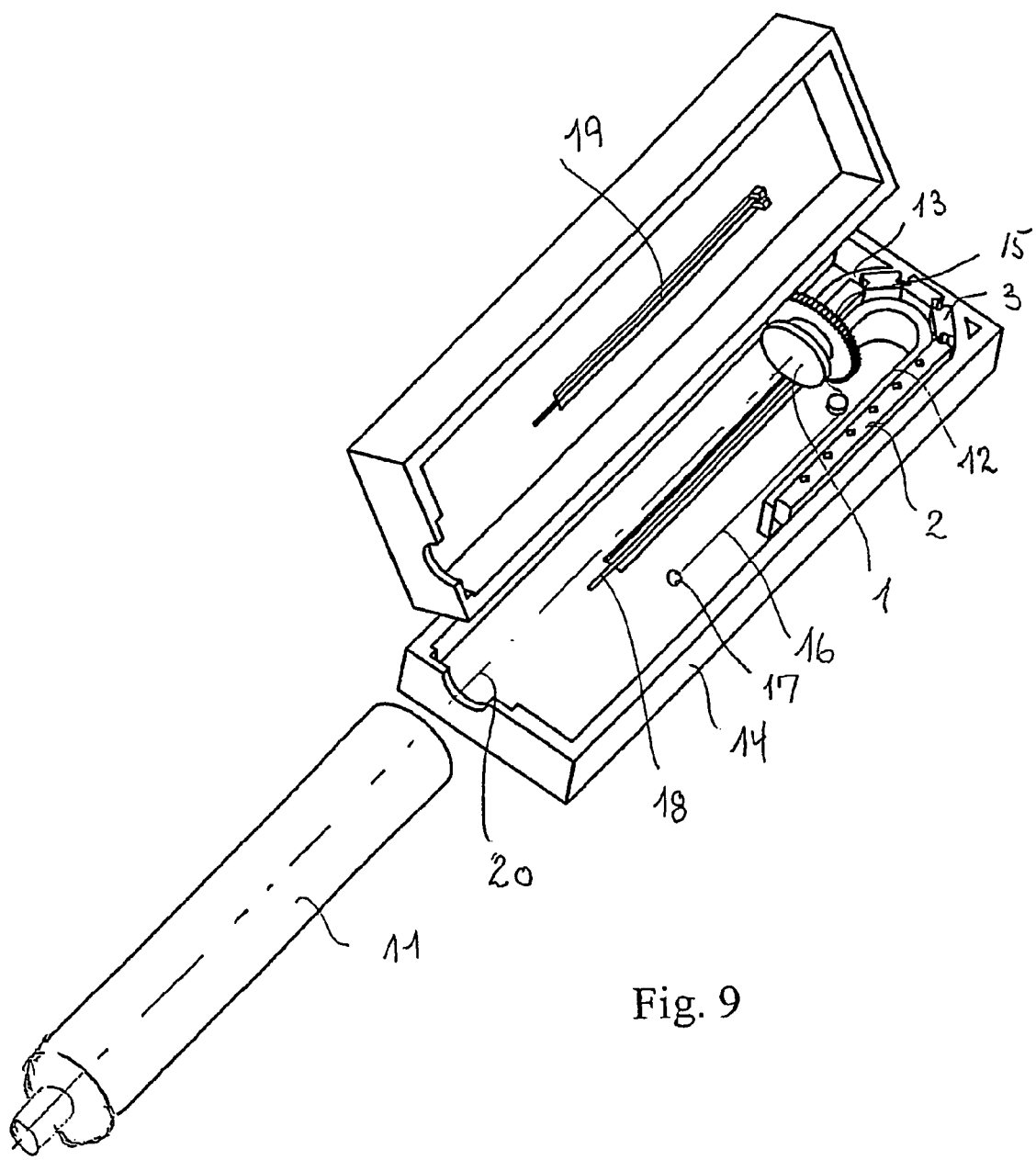
FIG. 9 is a schematic isometric view of a medicine dispensing device incorporating a flexible piston rod as shown in FIG. 1.

This ability to curve allows the compact configuration of any device utilizing the flexible piston rod 2 to linearly displace an object because the initially major part of the piston rod may extend along the intended path of travel of the piston 1 during such displacement of said object, see FIG. 9 and the corresponding explanation.

The material of the flexible piston rod 2 may be any suitable moldable material, but it is preferred that it be a plastic material such as Nylon or POM. The elements, hinges and piston are molded in one piece in a single molding operation which reduces the manufacturing cost considerably.

Each element 3 is provided with exterior threads 6 on two opposed portions 7 and 8 of the elements having a circular cylindrical configuration. At least the side 9 of the elements 3 coinciding with the hinges 4 is flat to allow practical molding of the hinge. A further function of the flat side 9 or preferably two opposed flat sides 9 and 10 is to prevent rotation of the piston rod 2 around its axis when being axially displaced by the threads of an actuator meshing with the threads 6; see for instance FIG. 9.

Referring now to FIG. 9, the flexible piston rod 2 is shown in use for dispensing insulin from a carpule 11 shown before being placed in operational position for greater clarity and having a not shown internal piston for being abutted and displaced by the piston 1. The piston rod 2 is arranged for movement between two guide walls 12 and 13 in a housing 14 of the device. The piston 1 abuts the not shown displaceable wall or piston of the carpule 11 such that axial displacement of the piston 1 will press insulin out of the carpule 11 into a not shown needle for injection into a patient.

A gear 15 mounted for rotation in the housing 14 is provided with a central aperture through which the elements 3 of the piston extend. The internal aperture is provided with a not shown screw thread meshing with the screw thread 6 of the piston elements 3 such that rotation of the gear 15 entails displacement of the piston 1 into the carpule 11.

The gear 15 is rotated by a shape memory alloy actuator comprising a wire 16 of a shape memory alloy such as Nitinol, one end of which is attached to a rivet 17 and the other end of which is attached to the free end of an actuator spring rod 18.

The free end of the actuator spring rod 18 is located such that it meshes with the teeth of the gear 15 and is biased by the spring force of the rod to exert a spring force in the tangential direction and in the radial direction.

A pawl spring rod 19 is located such that the end thereof meshes with the teeth of the gear 15 and is biased to exert a spring force in the radial direction. This end of the pawl spring rod 19 is constrained to substantially only move in the radial direction by two not shown stop pins.

A not shown battery supplies power to the ends of the nitinol wire 16 for heating it so as to cause it to contract.

Rotation of the gear 15 is brought about by alternatingly heating and cooling the nitinol wire 16 so that it contracts and cocks the spring rod 18 while the pawl spring rod holds the gear 15 against rotation and thereafter expands and allows the spring rod to turn the gear and advance the piston rod 2.

The flat surfaces 9 and 10 of the elements 3 abut the flat surfaces of the guide walls 12 and 13 and prevent the piston rod 2 from rotating around the longitudinal axis 20 thereof under the influence of the rotating gear 15.

Figure 10:
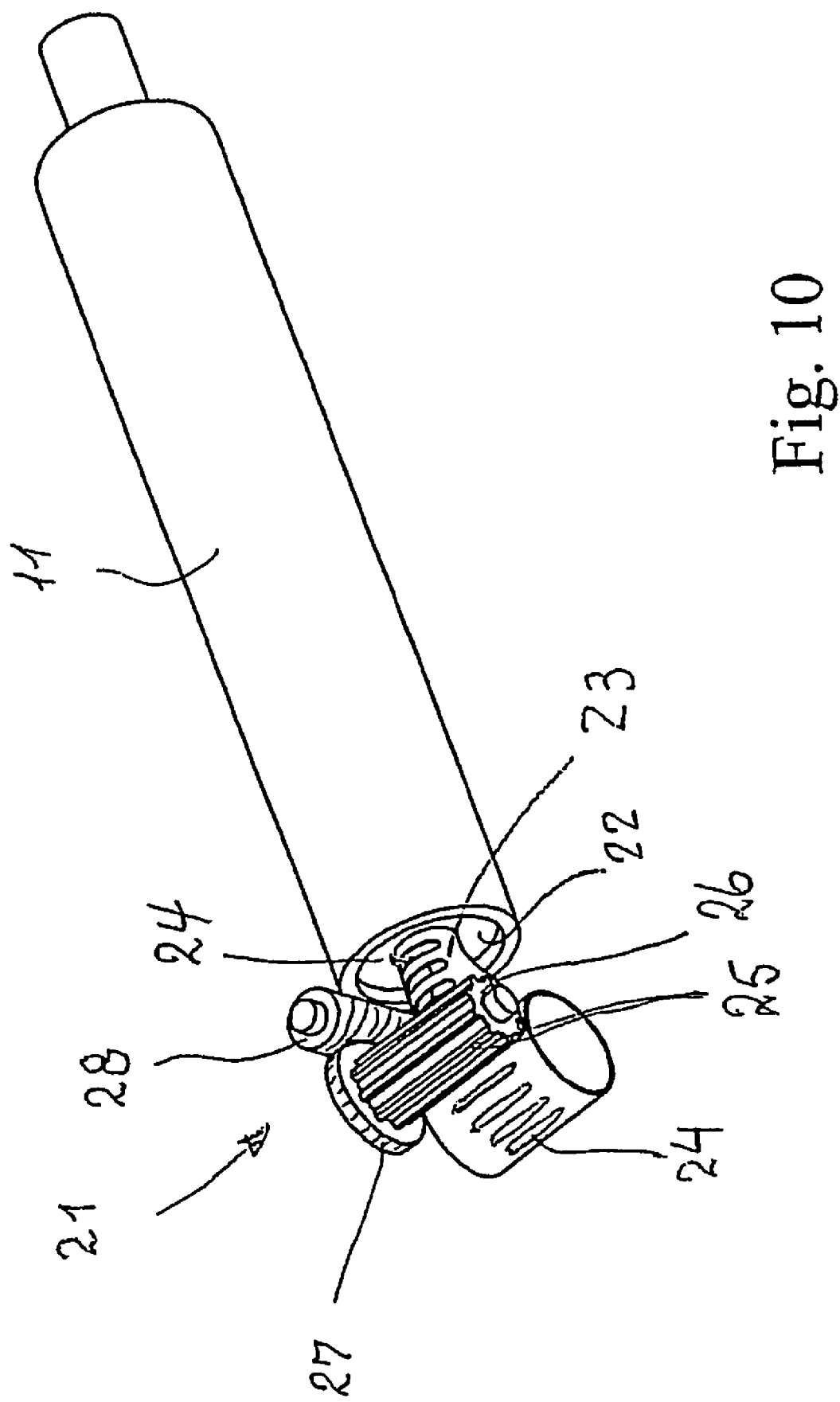
FIG. 10 is a schematic isometric view of second embodiment of a flexible piston rod applied to a medicine dispensing device.

The flexible piston rod 2 could also be displaced by means of another actuator, for instance a worm gear:

Referring now to FIG. 10, a carpule 11 identical to the one described in connection with FIG. 9 is located adjacent an actuator generally referenced by the numeral 21 with a piston 22 of the actuator abutting the not visible piston of the carpule.

The piston 22 is attached to the end of a steel strip 23 having an arcuate cross section taken at right angles to the longitudinal direction of the strip 23. This arcuate shape entails a rigidity of the strip 23 against lateral deflection such that the strip can transmit pressure forces to the piston 22 without collapsing because of lateral deflection.

A row of evenly spaced elongate apertures 24 are provided in the strip 23 for receiving ribs 25 of a roller 26 having a gear 27 meshing with a worm gear 28.

The worm gear is actuated by an actuator that may be similar to the shape memory alloy actuator of FIG. 9.

By rotating the worm gear 28 the gear 27 and roller 26 are rotated whereby the ribs 25 received in the apertures 24 unwind the strip 23 from the roll and displace it into the carpule 11 whereby the piston 22 displaces the carpule piston and dispenses the insulin from the carpule 11 that is located in the dispensing device in the same manner as the carpule 11 of FIG. 9.

The invention claimed is:

1. A flexible piston rod, particularly for use in medicine dispensing devices, comprising a row of elements each having a top surface and a bottom surface as well as lateral surfaces including a first and a second mutually opposed cylindrical surface portions extending in a generally longitudinal direction and incorporating an exterior thread pattern for meshing with a corresponding screw thread of an actuator for displacing the piston rod in the longitudinal direction thereof, the top surface of one element being connected to the bottom surface of the adjacent element by a hinge comprising an integral formation disposed between the top surface of the one element and the bottom surface of the adjacent element and being adapted to allow the two adjacent elements to pivot from a first position where at least a portion of a top surface of one element abuts a corresponding portion of the bottom surface of the adjacent element, said first position corresponding to a rectilinear, relatively stiff configuration of at least a portion of the piston rod, to a second position wherein said top surface of one element is spaced from said bottom surface of the adjacent element corresponding to a curved configuration of at least a portion of said flexible piston rod.

2. A piston rod according to claim 1, wherein at least one surface portions disposed between said first and second cylindrical surface portions is a plane so as to said actuator screw threads.

3. A piston rod according to claim 2, wherein said portions of said top and bottom surfaces are spaced from said hinge.

4. A piston rod according to claim 2, wherein said elements and said hinges form an integrally molded piston rod molded in one piece from a moldable plastic material.

5. A piston rod according to claim 1, wherein said portions of said top and bottom surfaces are spaced from said hinge.

6. A piston rod according to claim 5, wherein said elements and said hinges form an integrally molded piston rod molded in one piece from a moldable plastic material.

7. A piston rod according to claim 1, wherein said elements and said hinges form an integrally molded piston rod molded in one piece from a moldable plastic material.

8. A piston rod according to claim 7, wherein the moldable plastic material comprises a material selected from the group consisting of Nylon or POM.

9. A piston rod according to claim 1, wherein the hinge comprises integrally formed, bendable material extending in a direction generally away from the top surface of the one element and generally toward the bottom surface of the adjacent element.

10. A piston rod according to claim 1, wherein the exterior thread pattern is a discontinuous thread pattern.

* * * * *

UNITED STATES PATENT AND TRADEMARK OFFICE
CERTIFICATE OF CORRECTION

PATENT NO. : 7,220,248 B2  Page 1 of 1
APPLICATION NO. : 11/158277
DATED : May 22, 2007
INVENTOR(S) : Morten Mernoe It is certified that error appears in the above-identified patent and that said Letters Patent is hereby corrected as shown below:

Column 4, line 35, please delete "portions" and insert --portion-- therefor;

Column 4, line 36, after "to" please insert --allow co-operation with means to prevent rotation of the piston rod around the longitudinal axis thereof when said exterior thread pattern meshes with--;

Column 4, line 38, please delete "2" and insert --1-- therefor;

Column 4, line 40, please delete "2" and insert --1-- therefor;

Column 4, line 43, please delete "1" and insert --2-- therefor;

Column 4, line 45, please delete "5" and insert --2-- therefor;

Column 4, line 48, please delete "1" and insert --3-- therefor;

Column 4, line 52, please delete "7" and insert --4-- therefor.

Signed and Sealed this

Second Day of September, 2008

JON W. DUDAS
*Director of the United States Patent and Trademark Office*